US00PP21860P2

(12) United States Plant Patent
Egger

(10) Patent No.: US PP21,860 P2
(45) Date of Patent: Apr. 5, 2011

(54) ***HEUCHERA* PLANT NAMED 'MINT JULEP'**

(50) Latin Name: ***Heuchera* hybrid**
Varietal Denomination: Mint Julep

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 36 days.

(21) Appl. No.: 12/653,602

(22) Filed: Dec. 14, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner* — Kent L Bell
(74) *Attorney, Agent, or Firm* — Klarquist Sparkman, LLP

(57) ABSTRACT

A new and distinct *Heuchera* plant characterized by medium yellow-lime to lime-colored leaves with prominent veins, white flowers on a short flowering stems, excellent vigor, and excellent tolerance to heat and humidity.

1 Drawing Sheet

Botanical denomination: *Heuchera* hybrid.
Variety designation: 'Mint Julep'.

BACKGROUND OF THE INVENTION

The present invention relates to a new and distinct cultivar of *Heuchera* hybrid and given the cultivar name of 'Mint Julep'. *Heuchera* is in the family *Saxifragaceae. Heuchera* 'Mint Julep' originated from a cross between *Heuchera* 834-13, a proprietary, unreleased selection, as the seed parent, and *Heuchera* 749-8, a proprietary unreleased plant, as the pollen parent.

Compared to the seed parent, *Heuchera* 834-13, the new cultivar has short white rather than tall pink to white flowers and lime green rather than rose to olive green leaves.

Compared to the pollen parent, *Heuchera* 749-8, the new cultivar has lime green rather than brown leaves.

Compared to *Heuchera* 'Mint Frost', an unpatented plant, the new cultivar has yellow lime to lime colored leaves rather than green leaves. The new cultivar has more crowns.

This new *Heuchera* is distinguished by:

1. medium yellow lime to lime colored leaves,
2. leaves with prominent veins,
3. white flowers on a short flowering stems,
4. excellent vigor,
5. excellent tolerance to heat and humidity.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows three nine-month-old plants of *Heuchera* 'Mint Julep' grown in one gallon pots in a cool greenhouse in the spring in Canby, Oreg.

FIG. 2 shows a one-year-old plant in August in the garden in Canby, Oreg.

DETAILED PLANT DESCRIPTION

The following is a detailed description of the new *Heuchera* cultivar based on observations taken in May of nine-month-old specimen grown in a one gallon container in a cool greenhouse in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 5th edition.

Plant:

*Form.*—Basal rosette, herbaceous perennial.
*Hardiness.*—USDA Zone 4 to 9.
*Size.*—9 cm tall from top of the foliage to the ground and 25 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Basal.
*Shape.*—Broadly ovate.
*Lobing/division.*—7 shallow lobes, the terminal is the longest.
*Venation.*—Palmate.
*Margins.*—Crenate.
*Apex.*—Mucronulate.
*Base.*—Cordate, lobes sometimes overlapping slightly at the base.
*Blade size.*—9 to 12 cm long and 8.5 to 10 cm wide.
*Surface texture.*—Glandular on both sides.
*Petiole description.*—6 cm long and 2.5 mm wide, glandular hairs, Yellow Green 145A.
*Leaf color.*—Spring topside is Yellow Green 145C with veins Yellow Green 145A, bottom side Yellow Green 145C; summer to winter leaves are more lime, between. Yellow Green 144A and Greyed Green 193A with veins Yellow Green 144A, bottom side Green 139D.

Inflorescence:

*Size.*—Grows to 14 cm long and 3.5 cm wide.

*Type.*—Thyrse.

*Number of flowers per thyrse.*—About 80 per thyrse.

*Number of thyrse.*—About 5 to 8 in spring bloom.

*Peduncle.*—Grows to 34 cm tall, 3 mm wide at base, Yellow Green 145A, prominent glandular hairs, with 0 to 2 cauline leaves (grow to 4 cm long and 2 cm wide, ovate, with 3 main lobes, margin crenate, tip mucronulate, base cordate, glandular on both sides, topside Yellow Green 145C with veins Yellow Green 145A, bottom side Yellow Green 145C).

*Pedicel.*—Variable in size, with glandular hairs, Yellow Green 145A.

*Bloom period.*—Late May to June in Canby, Oreg.

Flower bud:

*Size.*—3 mm wide and 3.5 mm long.

*Description.*—Glandular puberulent, ovoid.

*Color.*—Yellow 4D.

Flower:

*Type.*—Perfect.

*Shape.*—Campanulate.

*Size.*—5 mm long and 3.5 mm wide.

*Petal description.*—5 in number, insignificant, reflexed, 1.8 mm long, lanceolate, tip acute, margin entire, glabrous on top side and glandular on bottom side, White NN155D on both sides.

*Calyx description.*—Campanulate, 5 mm long and 3 mm wide, with 5 lobes, divided ½ way to the base, acute, entire, glandular hairs on outside, glabrous inside; inside and outside color White NN155D except at tip and base where Green Yellow 1C.

*Stamen description.*—5 in number, filaments 1.5 mm long, White NN155D, anthers sterile, 0.4 mm, Greyed Orange 177B.

*Pistil description.*—1, 2-beaked, 3.5 mm long, ovary 1.5mm, Yellow 8D, style 2 mm long, NN155D.

*Fragrance.*—None.

*Lastingness.*—Each thyrse blooms for about 2 weeks on the plant.

Fruit:

*Type.*—Two beaked capsule.

*Size.*—3.5 mm deep by 5 mm wide.

*Fertility.*—Poor.

*Color.*—Brown 200D.

Seed: none seen.

Pest and disease tolerance: Excellent disease resistance to powdery mildew, the common problem of *Heuchera*. Susceptible to *Heuchera* rust and root weevils.

I claim:

1. A new and distinct hybrid of *Heuchera* plant as herein illustrated and described.

* * * * *

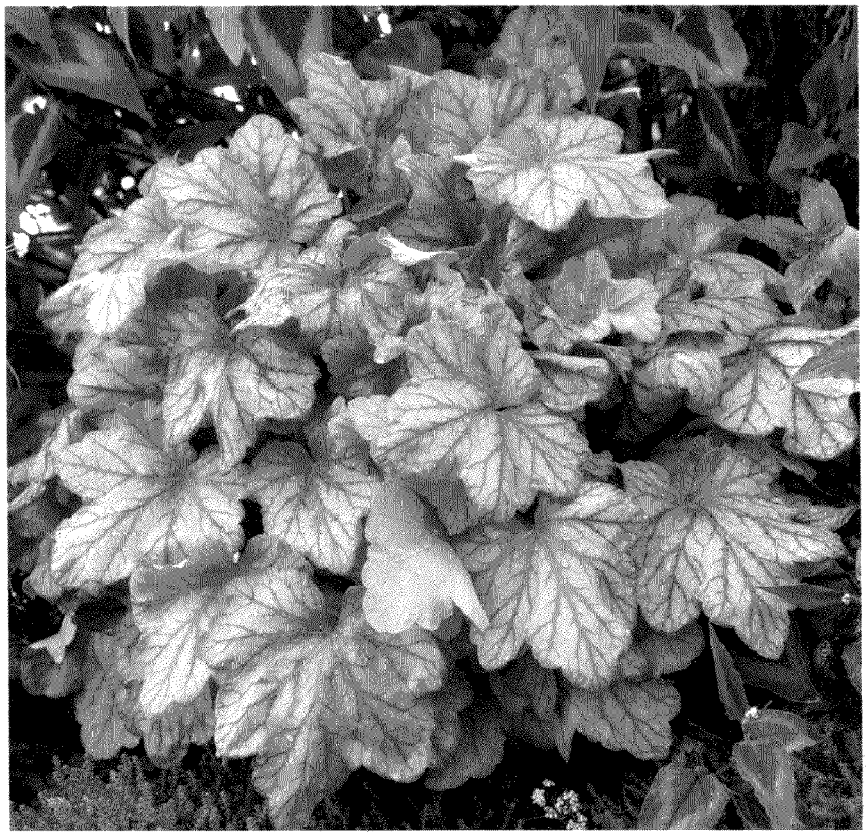

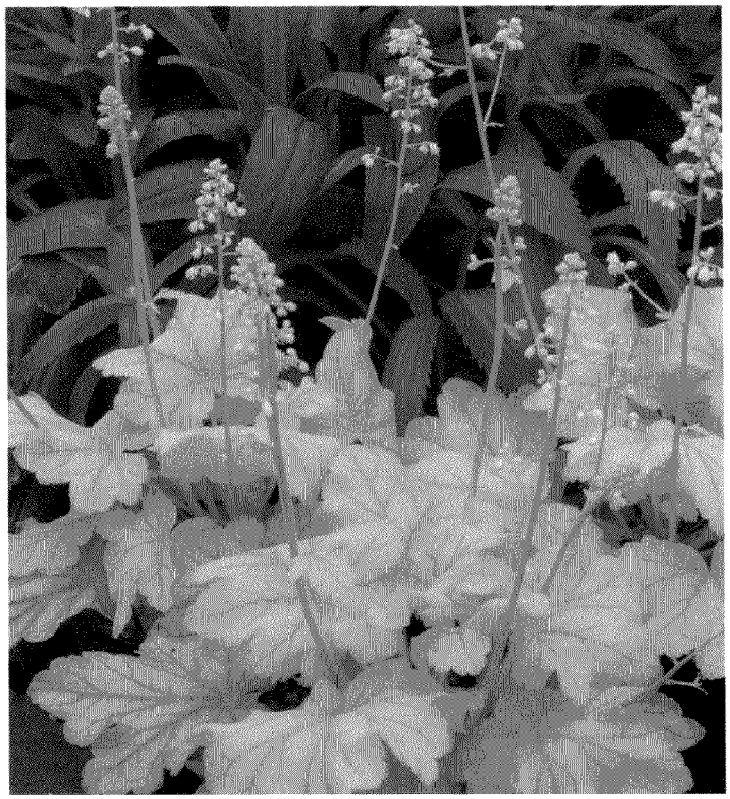
Figure 1 above, Figure 2 below